(12) United States Patent
Fima et al.

(10) Patent No.: US 11,911,432 B2
(45) Date of Patent: Feb. 27, 2024

(54) METHODS AND SYSTEMS FOR PRODUCING EMULATED HONEY

(71) Applicant: BEE-IO HONEY TECHNOLOGIES, LTD., Rehovot (IL)

(72) Inventors: Sharon Fima, Kfar Hanagid (IL); Lior Yedidya, Jerusalem (IL); Lena Birger, Netanya (IL)

(73) Assignee: BEE-IO HONEY TECHNOLOGIES, LTD., Rehovot (IL)

( * ) Notice: Subject to any disclaimer, the term of this patent is extended or adjusted under 35 U.S.C. 154(b) by 0 days.

(21) Appl. No.: 17/767,301

(22) PCT Filed: Jan. 3, 2022

(86) PCT No.: PCT/US2022/011038
§ 371 (c)(1),
(2) Date: Apr. 7, 2022

(87) PCT Pub. No.: WO2022/155021
PCT Pub. Date: Jul. 21, 2022

(65) Prior Publication Data
US 2023/0338456 A1    Oct. 26, 2023

Related U.S. Application Data

(60) Provisional application No. 63/133,577, filed on Jan. 4, 2021.

(51) Int. Cl.
| | | |
|---|---|---|
| *A61K 36/81* | (2006.01) | |
| *A23L 21/25* | (2016.01) | |
| *A61K 36/185* | (2006.01) | |
| *A61K 36/27* | (2006.01) | |
| *A61K 36/34* | (2006.01) | |
| *A61K 36/51* | (2006.01) | |
| *B04B 5/00* | (2006.01) | |
| *B04B 11/06* | (2006.01) | |

(52) U.S. Cl.
CPC .............. *A61K 36/81* (2013.01); *A23L 21/27* (2016.08); *A61K 36/185* (2013.01); *A61K 36/27* (2013.01); *A61K 36/34* (2013.01); *A61K 36/51* (2013.01); *B04B 5/00* (2013.01); *B04B 11/06* (2013.01); *A61K 2236/33* (2013.01); *A61K 2236/331* (2013.01); *A61K 2236/37* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | |
|---|---|---|
| 2008/0181821 A1 | 7/2008 | Jung et al. |
| 2013/0130243 A1 | 5/2013 | Livache et al. |
| 2014/0349279 A1 | 11/2014 | Berthelot et al. |
| 2020/0030347 A1 | 1/2020 | Kershaw et al. |
| 2020/0359669 A1 | 11/2020 | Ho |

FOREIGN PATENT DOCUMENTS

CN     108783350 A  * 11/2018

* cited by examiner

*Primary Examiner* — Michael V Meller
(74) *Attorney, Agent, or Firm* — Guy Levi; The IP Law Firm of Guy Levi, LLC

(57) ABSTRACT

The disclosure relates to methods, systems and compositions for producing emulated honey. More specifically, the disclosure relates to systems, compositions and methods for semi-continuously producing emulated honey using pressure-driven fluidic platforms comprising a plurality of microfluidic and/or milifluidic devices containing fluidic unit operations operable to convert plant nectar to emulated honey.

7 Claims, 2 Drawing Sheets

METHODS AND SYSTEMS FOR PRODUCING EMULATED HONEY

CROSS REFERENCE TO RELATED APPLICATIONS

This patent application is a U.S. National Phase filing of commonly owned and pending PCT Application No. PCT/US22/011038, filed Jan. 3, 2022, which is based on and claims the benefit of the filing date of now expired U.S. Provisional Patent Application Ser. No. 63/133,577, filed Jan. 4, 2021, both which are incorporated herein by reference in their entirely.

BACKGROUND

The disclosure is directed to methods, systems and compositions for producing emulated honey. More specifically, the disclosure is directed to systems, compositions and methods for semi-continuously producing emulated honey using microfluidic platforms.

Honey is a product containing about 40% fructose and 40% glucose, and a number of mineral and vitamin supplements, including potassium, chlorine, sulphur, calcium, sodium, phosphorus, magnesium, silicon, iron, manganese, copper, nickel, boron, aluminium and iodine. It also contains traces of Vitamin A, Vitamins B and B-Complex, and Vitamins D and E.

Honey has been used in medicine since ancient ages and its healing effects on wounds in humans was documented already by the Egyptians at 2000 B.C. Presently, honey's therapeutic properties besides osmolarity and acidity, are explained by the hydrogen peroxide content as an action of peroxidase oxidase (White, et al. 1963 *Biochem Biophys Acta* 73, 57-70), the origin of the nectar by its different flavonoid and phenolic acids content (Taormina, et al. 2001. *Int J Food Microbiol* 69 (3), 217-225; Wandan, H. A. 1998. *Infection* 26 (1), 26-31), and an unidentified component (Molan, P. C. 2001. World Wide Wounds (online); Available from URL: http://www.worldwidewounds.com/2001/november/Molan/honey-as-topical-agent.html). Despite scientific efforts performed during the last 30 years (Lusby, P. E., et al. 2005 *Arch Med Res* 36 (5), 464-467; Molan, P. C. 2006. *Int J Low Extrem Wounds* 5 (1), 40-54 *Int J Low Extrem Wounds* 5 (2), 122; Mundo, M. A., et al. 2004 *Int J Food Microbiol* 1, 97 (1), 1-8) the mystery regarding many of honey's modes of action still remains to be solved.

In addition, honey revealed moderate antitumor and pronounced antimetastatic effects when tested in rats; the antitumor activity of 5-fluorouracil and cyclophosphamide is potentiated by honey. Scientific literature has also suggested honey applications for treating cardiovascular diseases, cataracts and bronchial asthma and for preserving graft tissues. Further, honey has proven effective in treating cold sores and herpes simplex on the lips, skin allergies and insect bites. Additional use of honey as an alternative to artificial sweeteners in various end-use industries as well as its increase use in the cosmetics and medical industry leads to increase demand.

With projected worldwide CAGR of 8.0% between 2019 and 2025, the need exists for methods, systems and compositions for producing commercially viable amounts of emulated honey for further processing and use.

SUMMARY

Disclosed, in various implementations, are methods, systems and compositions for producing emulated honey. In other exemplary implementations, provided herein are systems, compositions and methods for semi-continuously producing emulated honey using microfluidic platforms.

In an exemplary implementation, provided herein is a pressure driven microfluidic platform for ex-vivo production of emulated honey, the platform comprises: a pressurized plant nectar reservoir; a plurality of microfluidic devices (MFD), operable to convert the nectar to emulated honey each microfluidic device further defining a longitudinal axis $X_L$ and being in fluid communication with the pressurized plant nectar reservoir; and an emulated honey collection vessel in fluid communication with each microfluidic device.

In another exemplary implementation, provided herein is a method of producing emulated honey, implemented in a system comprising: a pressurized plant nectar reservoir, a plurality of microfluidic devices (MFD), operable to convert the nectar to emulated honey each microfluidic device further defining a longitudinal axis $X_L$ and being in fluid communication with the pressurized plant nectar reservoir, and an emulated honey collection vessel in fluid communication with each microfluidic device, the method comprising: using the pressurized plant nectar reservoir, contacting the MFD with nectar stored in the pressurized plant nectar reservoir; using the MFD, converting the nectar to emulated honey; and collecting the emulated honey in the emulated honey collection vessel.

BRIEF DESCRIPTION OF THE FIGURES

For a better understanding of the systems, compositions and methods for semi-continuously producing ex-vivo emulated honey, reference is made to the accompanying examples and figures, in which.

DETAILED DESCRIPTION

Provided herein are exemplary implementations of methods, systems and compositions for producing semi-continuously producing emulated honey using microfluidic platforms (MFP). Although typically, the term 'microfluidic' means systems or devices having a network of processing nodes, chambers and reservoirs connected by channels, in which the channels have typical cross-sectional dimensions in the range between about 1.0 µm and about 500 µm, where channels having these cross-sectional dimensions are referred to as 'microchannels', in the disclosure, the term microfluidic refers generally to systems or devices having a network of processing nodes, chambers and reservoirs connected by channels that are also 'milifluidic', having channels with about 1 mm width.

Figure 1:
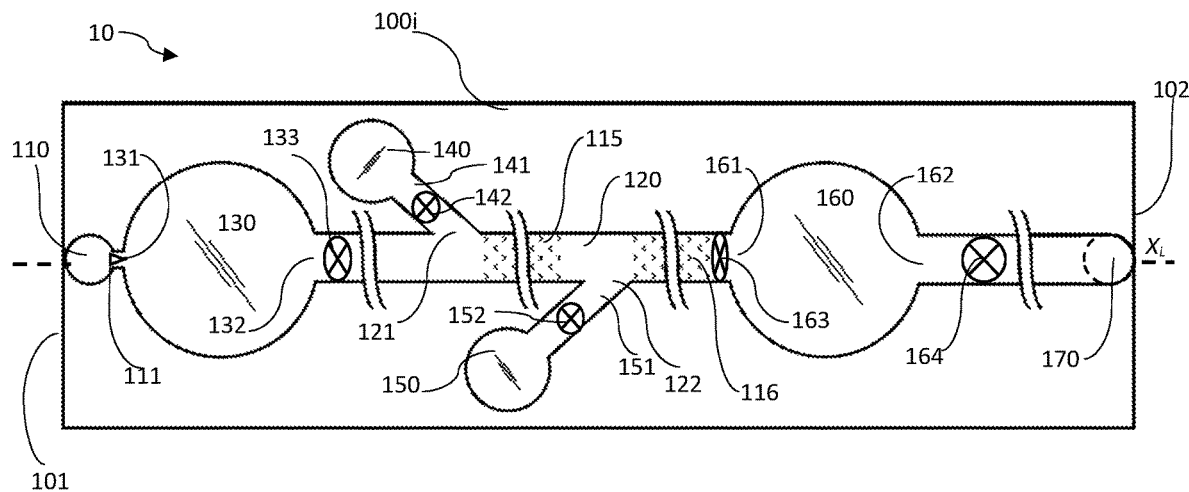
FIG. 1, is a top plan view schematic of an exemplary implementation of the microfluidic device (MFD) used to implement the methods disclosed.
Figure 2:
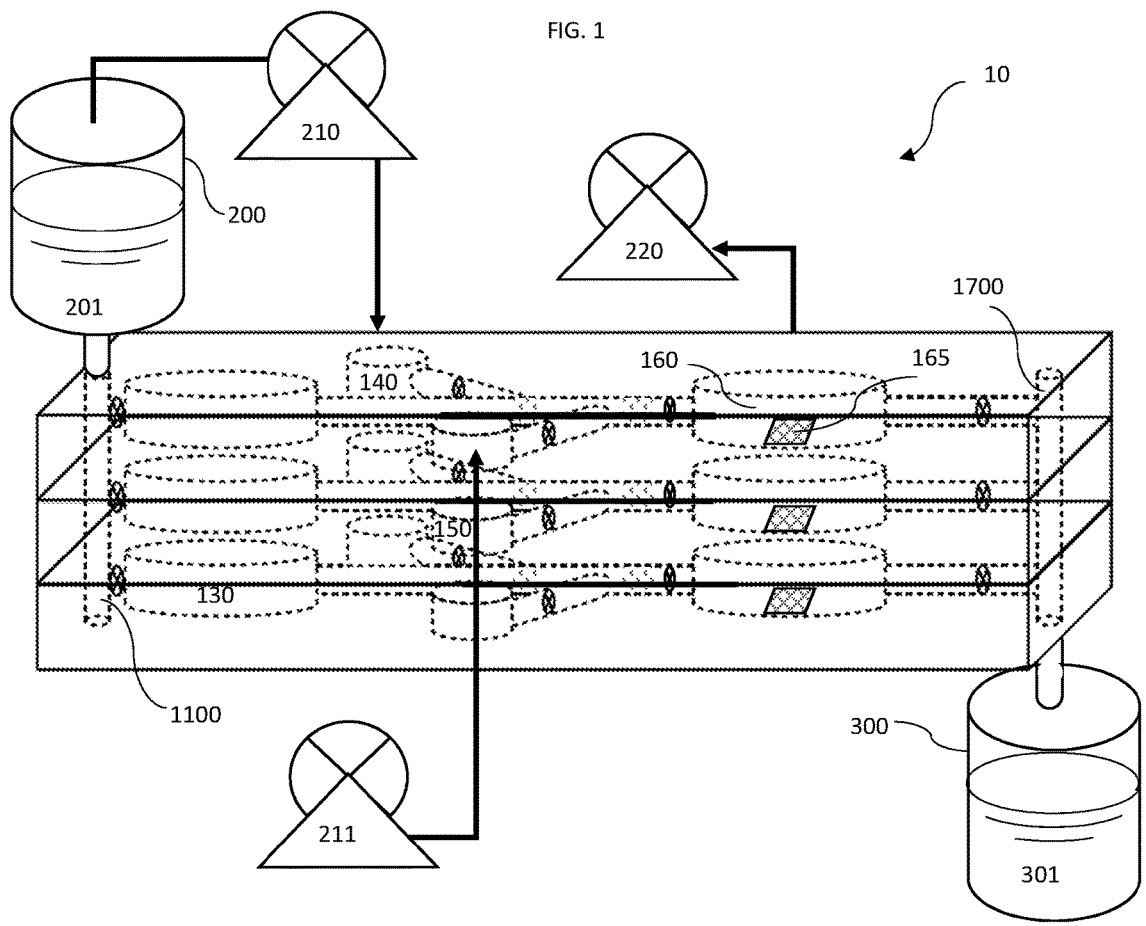
FIG. 2, is a schematic of an exemplary implementation of the microfluidic platform (MFP) with the array of stacked MFDs.

In an exemplary implementation, the microfluidic platform (MFP) provides a set of fluidic unit operations encompassed for example by the microfluidic device illustrated in FIGS. 1, and 2, which are sized and adapted for easy combination using well-defined fabrication technology to form a larger unit operation. This MFP thus enables implementation of different application-specific biochemical processes with well-defined controls and minimization of batch contamination. The microfluidic platforms disclosed, used to implement the methods described enable the miniaturization, integration, automation and parallelization (scalability) of biochemical processes such as production of emulated honey from plant nectar in an easy, consistent and repeatable manner. In the context of the disclosure then, the term "microfluidic platform" (MFP) means a set of fluidic unit operations, which are designed for easy combination within a well-defined fabrication technology. Likewise, in the context of the disclosure, the term "emulated honey" means plant nectar that has undergone a a biochemical process resulting in a composition as well as other physico-chemical and organoleptic characteristics that is substantially equivalent to that of honey.

In an exemplary implementation, the MFP used to implement the methods described, with the compositions disclosed employs large scale integration of a microfluidic channel circuitry (in other words, a network of interconnected channels), with integrated microvalves based, for example on flexible membranes between a liquid-guiding conduit and a pneumatic control-channel layer in communication with the liquid-guiding channels. The microvalves are operable between closed or open position corresponding to, in certain configurations, the pneumatic pressure applied to the control-channels. In certain implementations, by combining several microvalves, more complex units like micropumps, in-line static mixers, multiplexers, etc. can be built up with a plurality of unit operations (see e.g., FIG. 1) on one single MFD.

Accordingly and in an exemplary implementation, provided herein is a pressure driven microfluidic platform for ex-vivo production of emulated honey, the platform comprises: a pressurized plant nectar reservoir; a plurality of microfluidic devices (MFD), operable to convert the nectar to emulated honey each microfluidic device further defining a longitudinal axis $X_L$ and being in fluid communication with the pressurized plant nectar reservoir; and an emulated honey collection vessel in fluid communication with each microfluidic device. The fluid communication is operable to provide laminar flow of the liquid composition within the channels, and through any in-line static mixers and micropumps provided. The pressure driven laminar flow platform comprises therefore liquid transport mechanisms based on pressure gradients, configured to provide hydrodynamically stable laminar flow profiles in micro/milli channels. In exemplary implementations external or internal pressure sources, such as syringes, pumps or micropumps, gas expansion principles, pneumatic displacement of membranes, and the like are used. In certain exemplary implementations, the plant nectar, the conversion composition, and the processing compositions, as well the final emulated honey are actuated by injecting them into the MFD inlets either in a batch-wise manner, or in a continuous mode, while controlling various check valves and shut-off valves as needed.

Accordingly and in an exemplary implementation, and as illustrated schematically in FIGS. 1, and 2, provided herein is pressure driven microfluidic platform 10 for ex-vivo production of emulated honey, the platform comprises: pressurized plant nectar reservoir 200 (See e.g., FIG. 2); a plurality of microfluidic devices (MFD) 100$i$, operable to convert the nectar to emulated honey, each microfluidic device 100$i$ further defining a longitudinal axis $X_L$ and being in fluid communication with pressurized plant nectar reservoir 200; and emulated honey collection vessel 300 in fluid communication with each microfluidic device.

As illustrated further in FIG. 1, each MFD 100 comprises: first bore 110 defined in a posterior end 101 of MFD 100, in laminar liquid communication with pressurized plant nectar reservoir 200 (See e.g., FIG. 2); first receptacle 130, configured to receive a predetermined amount of plant nectar composition 201 from pressurized plant nectar reservoir 200, first receptacle 130 being in laminar liquid communication with first bore 110; microfluidic conduit (MFC) 120 in laminar liquid communication with first receptacle 130; pressurized conversion receptacle 140, in laminar liquid communication with MFC 120, adjoined via channel 141 to MFC 120 at first junction 121 downstream (anteriorly) from first receptacle 130; pressurized processing receptacle 150, in laminar liquid communication with MFC 120 via channel 151, adjoined to MFC 120 in second junction 122 downstream from pressurized conversion receptacle 140; concentrating receptacle 160, having outlet 162 and inlet 161, inlet 161 being in laminar liquid communication with MFC 120 and adjoined to MFC 120 downstream from pressurized processing receptacle 150; and second bore 170, defined in anterior end 102 of MFD 100, in liquid communication with outlet 162 of concentration receptacle 160; and emulated honey collection vessel 300 (see e.g., FIG. 2)

Accordingly, the systems, devices and platforms disclosed and used to implement the methods provide a set of microfluidic (or milifluidic) elements, wherein each element being operable to perform a certain basic fluid handling step or unit operation. These basic unit operations are the building blocks for performing the methods disclosed herein and each unit operation (e.g., conversion, processing, and concentration) comprise at least one of: fluid transport, fluid metering, fluid mixing, valving, and concentration of various liquid compositions and plant nectar. As illustrated further in FIG. 2, MFP 10 comprises a plurality of MFD(s) 100, each with various microfluidic (or milifluidic, or generally fluidic) unit operations that can selectably combined (or removed) and thereby enable easy implementation of application-specific bioreactor within MFP 10. In the context of the disclosure, the term "microfluidic element" means a component in a microfluidic, milifluidic or fluidic system for performing a microfluidic function, such as, for example, at least one of: passive check valves, active valves, pressure sensors, connecting channels, membrane filtration units, threaded taps for external connecting tubes, compression chambers, pumps, and others that may be known to those of ordinary skill in the art. Single plant nectar reservoir 200 can, using feed manifold 1100 a plurality of MFD 100 units, and collect the product using collection manifold 1700.

So, turning back to FIG. 1, each MFD 100 further comprises: check valve 111 disposed between first bore 110 and first receptacle 130; first flow valve 142 operable between closed position and an open position, disposed between pressurized conversion receptacle 140 and MFC 120; second flow valve 152 operable between closed position and an open position, disposed between pressurized processing receptacle 150 and MFC 120; first shut-off valve 163 operable between closed position and an open position, disposed upstream from inlet 161 of concentrating receptacle 160; and shut-off valve 164, operable between closed position and an open position, disposed between concentrating receptacle outlet 162 and second bore 170.

The shut-off valves used in certain exemplary implementations, can utilize passive microvalves, comprising a flow regulating valve and a check valve, which together are operable to provide flow rates of between about 0.1 ml/s and 3.0 ml/s, with inlet pressure in MFC 120 maintained in a range of between about 50 kPa to 200 kPa (above atmospheric pressure at the operating temperature i.e. about 101.3

KPa). For example, shut off valve(s) 142, 152 can be comprised of two chambers separated by a membrane (e.g., PDMS membrane) coupled to an obstruction operable, upon application of pressure from, for example, a pneumatic pump, solenoid and the like, to bias the obstruction into channel 141 (151) and regulate (or shut off) liquid flow in the channel.

In the context of the disclosure, the terms "microfluidic conduit", "channel" and "flow channel" means a pathway formed in or through a medium that allows for movement of fluids, such as liquids and gases. In an exemplary implementation, channel/conduits in MFD 100 have cross-sectional dimensions in the range between about 1.0 μm and about 3000 μm, for example, between about 50.0 μm and about 1500 μm. The ranges are intended to include the above-recited values as upper or lower limits. The flow channel can have any selected shape or arrangement, examples of which include a linear or non-linear configuration, undulating, and a U-shaped configuration.

MFD 100, used in MFP 10 in the systems provided further comprises: first in-line mixer 115 disposed in MFC 120 downstream from first junction 121; and second in-line mixer 116 disposed in MFC 120 downstream from the second junction 122.

In certain exemplary implementation, and as schematically illustrated in FIG. 2, concentrating receptacle 160 is operably coupled to at least one of: vacuum source 220; heating element 165; and a desiccating agent 250 (not shown)

Accordingly, concentrating the converted and processed plant nectar, comprises in an exemplary implementation exposing the nectar to a saturated salt solution (in other words, the desiccating agent), for example, once transferred from MFC 120, to concentration receptacle 160 and shut off valves 163, 164 are closed, heat exchanger 165 can be activated and simultaneously be maintained, under vacuum, such that mild heating, for example to temperatures between about 30° C. and about 45° C., will facilitate concentration of plant nectar 201. Alternatively, or additionally, the saturated salt solution used to concentrate plant nectar 201 comprises in certain exemplary implementations, Lithium Iodide (LiI), Lithium Chloride (LiCl), Zirconium Bromide (ZnBr$_2$), Lithium Bromide, or a solution comprising one or more of the foregoing. Moreover, the step of concentrating the processed plant nectar in the methods disclosed, implemented in the systems provided, comprises in an exemplary implementation, exposing plant nectar 201 to phosphorous pentoxide (P$_2$O$_5$).

The pressurized (in other words, receptacle/reservoir being maintained at a pressure higher than 1.1 Atm. (P>111.4 KPa)) conversion receptacle comprises a conversion composition operable to convert at least one of: a disaccharide a trisaccharide, and other oligosaccharides, into a composition comprising: between about 19% (w/w) to about 85% monosaccharides, between about 0.1% to about 28% disaccharides, and between about 0.1% and about 22% trisaccharide, with the remainder being water to 100%. The composition will depend on the source of plant nectar 201 used initially, for example, day-blossom flowers having extrafloral nectaries, such as, for example, *Petunia axillaris* (*p. axillaris*), *Petunia exserta* (*p. exserta*), *Mimulus cardinalis* (*m. cardinalis*), *Asclepius syriaca* (*a. syriaca*), *Lobelia cardinalis* (*l. cardinalis*), or *Palicourea heterochroma* (*p. heterochroma*), will have different initial composition of di-, tri, and other oligosaccharides, than night-blossoming flowers such as, for example, *Macrocarpaea noctiluca* (*m. noctiluca*), and *Macrocarpaea arborescens* (*m. arborescens*), which, in turn, will have different initial composition of di-, tri, and other oligosaccharides, than fruits, such as, for example, grapes, honeydew melon, peaches and the like.

In an exemplary implementation, the conversion composition comprises an invertase enzyme derived from a bee. For example, invertase can be found in the salivary and hypopharingeal glands in bees (*apis mellifera, apis dorseta*). Similarly, pressurized processing receptacle 150 comprises a composition operable to catalyze an oligosaccharide present in the plant nectar, and remove hydrogen peroxide from the converted nectar. Therefore, the processing composition comprises at least one of: an α-amylase enzyme, a glucose oxidase enzyme, and a catalase enzyme, each derived from a bee.

Figure 3:
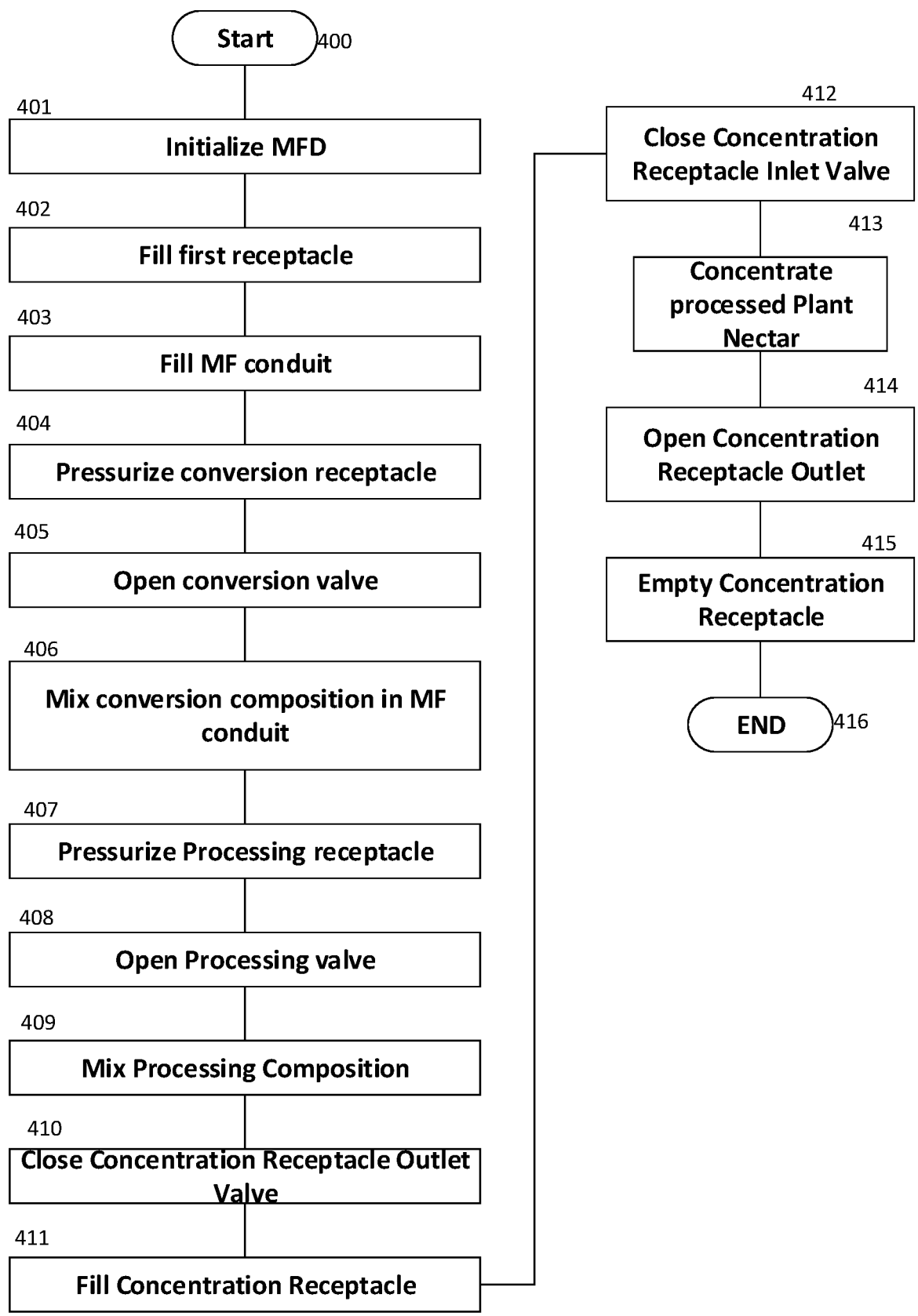
FIG. 3 is a flow chart of an exemplary implementation of the methods using the MFP to produce emulated honey.

In exemplary implementations, the microfluidic platforms utilizing the microfluidic (or milifluidic, or any properly sized fluidic) devices disclosed herein, are used to carry out the methods disclosed. Accordingly and in one such exemplary implementation, as illustrated in FIGS. 1-3, provided herein is a method of producing emulated honey, implemented in a system comprising: a pressurized plant nectar reservoir 200, a plurality of microfluidic devices (MFD) 100*i*, operable to convert plant nectar 201 to emulated honey, each microfluidic device 100*i* further defining longitudinal axis X$_L$ and being in fluid communication with pressurized plant nectar reservoir 200, and emulated honey collection vessel 300 in fluid communication with each microfluidic device 100*i*, the method comprising: using the pressurized plant nectar reservoir 200, contacting 401 MFD 100*i* with plant nectar 201 stored in pressurized plant nectar reservoir 200; using MFD 100*i*, converting 402-414 plant nectar 201 to emulated honey 301; and collecting emulated honey 301 in emulated honey collection vessel 300. More specifically, the method comprises, initializing 401 MFD 100*i* by opening first shut off valve 163 and closing second shut off valve 164; using pressurized nectar reservoir 200, filling 402 first receptacle 130 from first bore 110, wherein first receptacle 130 has inlet 131 in laminar liquid communication with first bore 110, and outlet 132 in laminar liquid communication with MFC 120 (MFC) 120; opening first receptacle flow valve 133, thereby using first receptacle, filling 403 MFC 120 with plant nectar 201; using e.g., micropump 210, pressurizing 404 conversion receptacle; opening 405 first flow valve 142; admixing 406 liquid composition operable to convert at least one of: a first disaccharide, and a first trisaccharide in plant nectar, to a composition comprising a monosaccharide, a second disaccharide and a second trisaccharide with plant nectar in MFC 120; using e.g., micropump 211, pressurize 407 processing receptacle 150; opening 408 second flow valve 152; admixing 409 liquid composition operable to catalyze an oligosaccharide in converted plant nectar, and remove hydrogen peroxide from converted nectar with converted nectar in MFC 120; validate closing 410 shut off valve 164 at outlet 162 of concertation receptacle 160; filling 411 concentrating receptacle 160 with processed plant nectar; closing 412 first shut-off valve 163; using for example, a combination of vacuum pump 220, heat exchanger 165, and desiccating agent 250 (not shown) concentrating 413 processed nectar to a predetermined concentration (w/w) of composition comprising a monosaccharide (e.g., glucose and fruictose), a second disaccharide (e.g., maltose, turanose, isomaltose, sucrose, maltulose, isomaltulose, nigerose, trigalose, gentabiose, laminaribiose) and a second trisaccharide (e.g., erlose, kestose, raffinos, dextrantriose, melezitose); opening 414 first and second shut-off valves 163, 164; and emptying 415 emulated honey 301 into emulated honey collection vessel 300.

In the context of the disclosure, the term "operable" means the system and/or the device (e.g., the nutrient dispensing pump) and/or the program, or a certain element, component or step is/are fully functional sized, adapted and calibrated, comprising elements for, having the proper internal dimension to accommodate, and meets applicable operability requirements to perform a recited function when activated, coupled or implemented, regardless of being powered or not, coupled, implemented, effected, actuated, realized or when an executable program is executed by at least one processor associated with the system, method, and/or the device.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

All ranges disclosed herein are inclusive of the endpoints, and the endpoints are independently combinable with each other. "Combination" is inclusive of blends, mixtures, alloys, reaction products, and the like. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the chamber (s) includes one or more chamber). Reference throughout the specification to "one implementation", "another implementation", "an exemplary implementation,", and so forth, when present, means that a particular element (e.g., feature, structure, and/or characteristic) described in connection with the implementation is included in at least one implementation described herein, and may or may not be present in other implementations. In addition, it is to be understood that the described elements may be combined in any suitable manner in the various implementations.

All ranges disclosed herein are inclusive of the endpoints, and the endpoints are independently combinable with each other. Furthermore, the terms "first," "second," and the like, herein do not denote any order, quantity, or importance, but rather are used to denote one element from another.

Likewise, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. For example, "about" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

Accordingly and in an exemplary implementation, provided herein is a pressure driven microfluidic platform for ex-vivo production of emulated honey, the platform comprises: a pressurized plant nectar reservoir; a plurality of microfluidic devices (MFD), operable to convert the nectar to emulated honey each microfluidic device further defining a longitudinal axis $X_L$ and being in fluid communication with the pressurized plant nectar reservoir; and an emulated honey collection vessel in fluid communication with each microfluidic device, wherein (i) each microfluidic device comprises: a first bore defined in a posterior end of the MFD, in liquid communication with the pressurized plant nectar reservoir; a first receptacle, configured to receive a predetermined amount of a nectar composition from the pressurized plant nectar reservoir, the first receptacle being in liquid communication with the first bore; a microfluidic conduit in liquid communication with the first receptacle; a pressurized conversion receptacle, in liquid communication with the microfluidic conduit, adjoined to the microfluidic conduit in a first junction downstream from the first receptacle; a pressurized processing receptacle, in liquid communication with the microfluidic conduit, adjoined to the microfluidic conduit in a second junction downstream from the pressurized conversion receptacle; a concentrating receptacle, having an outlet and an inlet, the inlet being in liquid communication with the microfluidic conduit and adjoined to the microfluidic conduit downstream from the pressurized processing receptacle; and a second bore, defined in an anterior end of the MFD, in liquid communication with the outlet of the concentration receptacle and the emulated honey collection vessel, as well as (ii) a check valve disposed between the first bore and the first receptacle; a first flow valve operable between a closed position and an open position, disposed between the pressurized conversion receptacle and the microfluidic conduit; a second flow valve operable between a closed position and an open position, disposed between the pressurized processing receptacle and the microfluidic conduit; a first shut-off valve operable between a closed position and an open position, disposed upstream from the inlet of the concentrating receptacle; and a shut-off valve operable between a closed position and an open position, disposed between the concentrating receptacle outlet and the second bore, and also (iii) a first in-line mixer disposed in the microfluidic conduit downstream from the first junction; and a second in-line mixer disposed in the microfluidic conduit downstream from the second junction, wherein (iv) the pressurized conversion receptacle and the processing receptacle are each operably coupled to a pump or a plunger, wherein (v) the concentrating receptacle is operably coupled to at least one of: a vacuum source; a heating element; and a desiccating agent, wherein (vi) the pressurized conversion receptacle comprises a conversion composition operable to convert at least one of: a disaccharide and a trisaccharide into a composition comprising: between about 19% (w/w) to about 85% monosaccharides, between about 0.1% to about 28% disaccharides, and between about 0.1% and about 22% trisaccharide, with the remainder being water to 100%, (vii) the conversion composition comprises an invertase enzyme derived from a bee, wherein (viii) the pressurized processing receptacle comprises a composition operable to catalyze an oligosaccharide, and remove hydrogen peroxide from the converted nectar, (ix) the composition comprises at least one of an α-amylase enzyme, a glucose oxidase enzyme, and a catalase enzyme, each derived from a bee, and wherein (x) the desiccating agent is a saturated salt solution of at least one of: Lithium Iodide (LiI), Lithium Chloride (LiCl), Zirconium Bromide ($ZnBr_2$), Lithium Bromide, and a solution comprising one or more of the foregoing, or Phosphorous Pentoxide ($P_2O_5$).

In another exemplary implementation, provided herein is a method of producing emulated honey, implemented in a system comprising: a pressurized plant nectar reservoir, a plurality of microfluidic devices (MFD), operable to convert the nectar to emulated honey each microfluidic device further defining a longitudinal axis $X_L$ and being in fluid communication with the pressurized plant nectar reservoir, and an emulated honey collection vessel in fluid communication with each microfluidic device, the method comprising: using the pressurized plant nectar reservoir, contacting the MFD with nectar stored in the pressurized plant nectar reservoir; using the MFD, converting the nectar to emulated honey; and collecting the emulated honey in the emulated honey collection vessel, wherein (xi) each microfluidic device comprises: a first bore defined in a posterior end of the MFD, in liquid communication with the pressurized plant nectar reservoir; a first receptacle, configured to receive a predetermined amount of a nectar composition from the pressurized plant nectar reservoir, the first receptacle being in liquid communication with the first bore; a microfluidic conduit in liquid communication with the first receptacle; a pressurized conversion receptacle, in liquid communication with the microfluidic conduit, adjoined to the microfluidic conduit in a first junction downstream from the first receptacle, wherein the conversion receptacle comprises a liquid composition operable to convert at least one of: a first disaccharide, and a first trisaccharide in the plant nectar, to a composition comprising a monosaccharide, a second disaccharide and a second trisaccharide; a pressurized processing receptacle, in liquid communication with the microfluidic conduit, adjoined to the microfluidic conduit in a second junction downstream from the pressurized conversion receptacle, wherein the processing receptacle comprises a liquid composition operable to catalyze an oligosaccharide in the converted plant nectar, and remove hydrogen peroxide from the converted nectar; a concentrating receptacle, having an outlet and an inlet, the inlet being in liquid communication with the microfluidic conduit and adjoined to the microfluidic conduit downstream from the pressurized processing receptacle; and a second bore, defined in an anterior end of the MFD, in liquid communication with the outlet of the concentration receptacle and the emulated honey collection vessel, wherein each microfluidic device comprises: (xii) a check valve disposed between the first bore and the first receptacle; a first flow valve operable between a closed position and an open position, disposed between the pressurized conversion receptacle and conduit; a second flow valve operable between a closed position and an open position, disposed between the pressurized processing receptacle and conduit; a first shut-off valve operable between a closed position and an open position, disposed upstream from the inlet of the concentrating receptacle; and a second shut-off valve operable between a closed position and an open position, disposed between the concentrating receptacle and the second bore, the method further comprising (xiii) opening the first shut off valve and closing the second shut off valve; using the pressurized nectar reservoir, filling the first receptacle from the first bore, wherein the first receptacle has an inlet in liquid communication with the first bore, and an outlet in liquid communication with the microfluidic conduit (MFC); opening the first flow valve, thereby using the first receptacle, filling the MFC with the plant nectar; opening the first flow valve; admixing the liquid composition operable to convert at least one of: a first disaccharide, and a first trisaccharide in the plant nectar, to a composition comprising a monosaccharide, a second disaccharaide and a second trisaccharide with the plant nectar in the MFC; opening the second flow valve; admixing the liquid composition operable to catalyze an oligosaccharide in the converted plant nectar, and remove hydrogen peroxide from the converted nectar with the converted nectar in the MFC; filling the concentrating receptacle with the processed plant nectar; closing the first shut-off valve; concentrating the processed nectar to a predetermined concentration (w/w) of composition comprising a monosaccharide, a second disaccharaide and a second trisaccharide; opening the first and second shut-off valves; and emptying the emulated honey into the emulated honey collection vessel, wherein (xiv) the liquid composition operable to convert at least one of: a first disaccharide, and a first trisaccharide in the plant nectar, to a composition comprising a monosaccharide, a second disaccharaide and a second trisaccharide comprises an invertase enzyme derived from a bee, (xv) operable to catalyze an oligosaccharide in the converted plant nectar, and remove hydrogen peroxide from the converted nectar comprises at least one of: an α-amylase enzyme, a glucose oxidase enzyme, and a catalase enzyme, each derived from a bee, wherein (xvi) the concentrating receptacle is operably coupled to at least one of: a vacuum source; a heating element; and a desiccating agent, whereby (xvii) the desiccating agent is a saturated salt solution of at least one of: Lithium Iodide (LiI), Lithium Chloride (LiCl), Zirconium Bromide ($ZnBr_2$), Lithium Bromide, and a solution comprising one or more of the foregoing, or Phosphorous Pentoxide ($P_2O_5$).

Although the foregoing disclosure for methods, systems and compositions for producing emulated honey. More specifically, the disclosure is directed to systems, compositions and methods for semi-continuously producing emulated honey using microfluidic platforms has been described in terms of some implementations, other implementations will be apparent to those of ordinary skill in the art from the disclosure herein. Moreover, the described implementations have been presented by way of example only, and are not intended to limit the scope of the inventions. Indeed, the novel methods, programs, libraries and systems described herein may be embodied in a variety of other forms without departing from the spirit thereof. Accordingly, other combinations, omissions, substitutions and modifications will be apparent to the skilled artisan in view of the disclosure herein.

What is claimed is:

1. A pressure driven microfluidic platform device for ex-vivo production of emulated honey comprising:
   a) a pressurized plant nectar reservoir;
   b) a plurality of microfluidic devices, operable to convert the nectar to emulated honey, each microfluidic device having an anterior end and a posterior end, and defining a longitudinal axis XL, and a first bore being in fluid communication with the pressurized plant nectar reservoir, and a second bore, in fluid communication with the emulated honey collection vessel, wherein each microfluidic device further comprises:
      i. a first receptacle, configured to receive a predetermined amount of a nectar composition from the pressurized plant nectar reservoir, the first receptacle being in liquid communication with the first bore;
      ii. a microfluidic conduit in liquid communication with and extending anteriorly from the first receptacle;
      iii. a pressurized conversion receptacle comprising a conversion composition with a bee derived invertase, in liquid communication with the microfluidic conduit, adjoined to the microfluidic conduit in a first junction downstream from the first receptacle;

iv. a pressurized processing receptacle containing a processing composition comprising at least one of an alpha-amylase enzyme, a glucose oxidase enzyme, and a catalase enzyme, each derived from a bee, the pressurized processing receptacle being in liquid communication with the microfluidic conduit, adjoined to the microfluidic conduit in a second junction downstream from the pressurized conversion receptacle; and v. a concentrating receptacle, having an outlet and an inlet, the inlet being in liquid communication with the microfluidic conduit and adjoined to the microfluidic conduit downstream from the pressurized processing receptacle, and the outlet being in liquid communication with the second bore; and c) an emulated honey collection vessel in fluid communication with each microfluidic device.

2. The platform of claim 1, wherein each microfluidic device further comprises:
a) a check valve disposed between the first bore and the first receptacle;
b) a first flow valve operable between a closed position and an open position, disposed between the pressurized conversion receptacle and the microfluidic conduit;
c) a second flow valve operable between a closed position and an open position, disposed between the pressurized processing receptacle and the microfluidic conduit;
d) a first shut-off valve operable between a closed position and an open position, disposed upstream from the inlet of the concentrating receptacle; and
e) a shut-off valve operable between a closed position and an open position, disposed between the concentrating receptacle outlet and the second bore.

3. The platform of claim 2, wherein each microfluidic device further comprises:
a) a first in-line mixer disposed in the microfluidic conduit downstream from the first junction; and
b) a second in-line mixer disposed in the microfluidic conduit downstream from the second junction.

4. The platform of claim 3, wherein the pressurized conversion receptacle and the processing receptacle are each operably coupled to a pump or a plunger.

5. The platform of claim 4, wherein the concentrating receptacle is operably coupled to at least one of:
a) a vacuum source;
b) a heating element; and
c) a desiccating agent.

6. The platform of claim 1, wherein the conversion composition converts at least one of: a disaccharide and a trisaccharide into a composition comprising: between about 19% (w/w) to about 85% monosaccharides, between about 0.1% to about 28% disaccharides, and between about 0.1% and about 22% trisaccharide, with the remainder being water to 100%.

7. The method of claim 5, wherein the desiccating agent is a saturated salt solution selected from the group consisting of Lithium Iodide (LiI), Lithium Chloride (LiCl), Zirconium Bromide ($ZnBr_2$), Lithium Bromide, Phosphorous Pentoxide ($P_2O_5$) and mixtures thereof.

* * * * *